United States Patent

Mous

[11] Patent Number: 5,769,829
[45] Date of Patent: Jun. 23, 1998

[54] CATHETER GUIDABLE BY MEANS OF FLOW

[75] Inventor: Frans Mous, Drachten, Netherlands

[73] Assignee: Cordis Corporation, Miami Lakes, Fla.

[21] Appl. No.: 755,498

[22] Filed: Nov. 22, 1996

[30]    Foreign Application Priority Data

Nov. 28, 1995 [NL]   Netherlands ............................ 1001763

[51] Int. Cl.[6] .................................................. A61M 25/00
[52] U.S. Cl. ............................................ 604/280; 604/53
[58] Field of Search ..................................... 604/280, 264, 604/53, 28; 128/656, 657, 658, 673

[56]              References Cited

U.S. PATENT DOCUMENTS 3,995,623  12/1976  Blake et al. ............................ 604/280
5,336,205   8/1994  Zenzen et al. .......................... 604/280

FOREIGN PATENT DOCUMENTS 0 488 021 A1  11/1991  European Pat. Off. .

*Primary Examiner*—John D. Yasko
*Attorney, Agent, or Firm*—Henry W. Collins

[57]                ABSTRACT

The invention relates to an endovascular non-balloon flow-directed catheter comprising a tube-like body with a proximal and a distal end, a connecting member connected to the proximal end, and a tube-like distal section which is very flexible and does not retain its shape when external forces are applied to the distal end. As a result this tube-like distal section is guided and carried along by the surrounding flow, in particular, by the flow of surrounding blood.

12 Claims, 2 Drawing Sheets

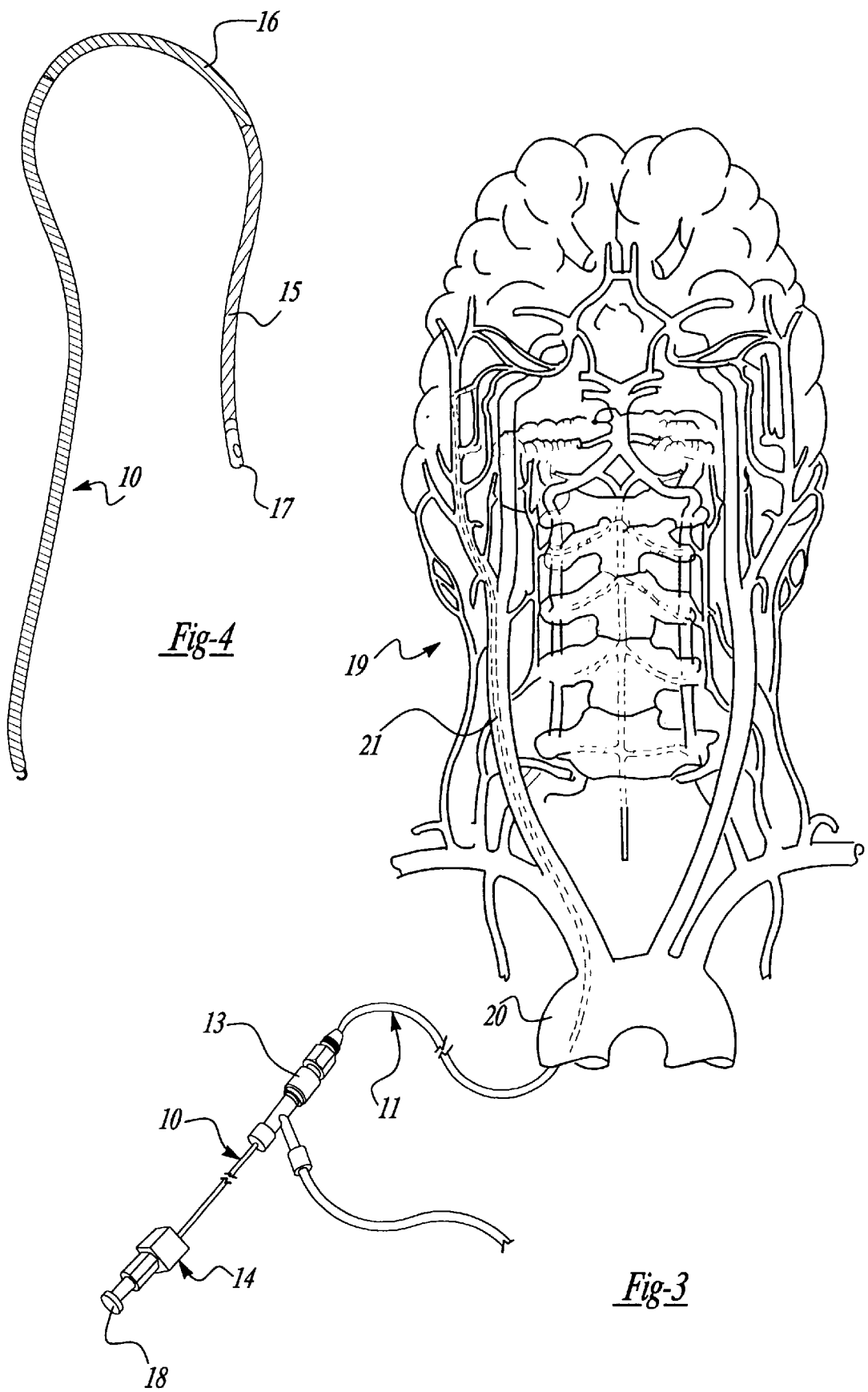

CATHETER GUIDABLE BY MEANS OF FLOW

FIELD OF THE INVENTION

This present invention relates to an endovascular catheter of a construction which permits the distal end to be directed to a selected location by the force of the flow of blood through the vessel.

BACKGROUND ART

Such catheters are generally known as "flow-directed" catheter and they generally include a balloon on the distal end of the catheter for directing the distal end along the vessel. Also, with other known endovascular catheters the distal end is preformed, so that the distal end will automatically assume a desired position in the area to be investigated or treated.

SUMMARY OF THE INVENTION

With the endovascular catheter according to the invention the tube-like distal section has been made pliable to such a degree that it does not retain its initial shape. As a result this tube-like distal end section is advanced and carried along by the surrounding blood flow.

Accordingly, the catheter will more or less automatically travel down the bloodstream in order to travel through the vessel in the desired position within the vessel.

The endovascular catheter according to the invention is particularly suitable for introduction into very small and tortuous blood vessels as may be found in the brain of a patient. In order to ensure that the catheter may be properly controlled, the distal end of the catheter is formed of a polymer having a modules of elasticity of less than 10 Newtons per square millimeters.

The distal section of the catheter can be given the desired greater flexibility by means of a suitable choice of material. Additionally, or instead of that, the distal end may be formed with very small diameter and of with very thin walls. With this construction the distal tip of the catheter will freely enter very small vessels.

The inner lumen of the catheter can consequently be made as large as possible, as a result of which the flow resistance to which a liquid flows through the lumen is subjected, can remain as low as possible.

Furthermore, the flow resistance to the flow of fluid through the inner lumen of the catheter is advantageous when positioning the catheter. When positioning the catheter short liquid pulses under high pressure may be injected into the catheter. As a result of the reactive force occurring at the end of the catheter, the distal end may be controlled in order to be positioned in the desired blood vessel. With this resistance to flow good maneuverability of the catheter may be achieved.

A very suitable embodiment of the endovascular catheter takes the form of a first section having an outside diameter of between 0.6 and 0.9 millimeter and a second section which is distal the first section which has an outer diameter of between 0.4 and 0.7 millimeter. In general, the second most pliable section is only a quarter of the length of the first section. Preferably, the first section of a length of between 10 and 30 centimeter and the second section is of a length of between 2 and 7 centimeters according to the invention may for instance be used for treatment of an embolization. An embolization medium such as cyano acrylate or ethanol any be supplied through the lumen.

For such an application the embodiment of the catheter according to the invention the first section of the catheter is constructed to have a burst pressure of 28 bar (200 psi) and the second section distal of the first section with a burst pressure of at least 27 bar (190 psi).

A suitable flexibility is obtained when the second section of the catheter (distal section) has a modules elasticity of approximately 10 Newton per square millimeter.

A suitable material of which to fabricate the catheter according to the invention is polyethylene elastomer (LDPE). Such a polyethylene-elastomer has a very dense molecular distribution, and therefore may be used for medical purposes. Furthermore, this material is inert to the action of the chemical substance to be used in conjunction with the catheter.

Another suitable material of which to fabricate the catheter of the present invention is polyvinyl chloride (pr) plasticized with polyurethane (PUR). In order to render this material more suitable for use with the substance mentioned, in particular cyano acrylate, a coating of polytetrafluroethane (PTFE). The cyano acrylate will not react with material so treated.

Yet another suitable material which may be used to fabricate the distal portion of the catheter is styrene ethyl block styrene polymer (SBSE). This material exhibits rubbery properties which is very suitable for the intended application.

In order to achieve optimum mechanical properties the catheter may be formed of a plurality of sections each of which is formed of a different material. These different materials can be incorporated in the distal section nu means of multi-layer co-extrusion or strip-shape extrusion.

It is also desirable to include an intermediate section in the catheter which has a flexibility greater than that of the proximal section and less than of the distal section. For the introduction as very then guidewire, which stiffens the very flexible distal section, may be used prior to inserting the catheter into the narrow blood vessels. The very flexible distal section can then be advanced further into the narrower blood vessels by means of the surrounding flow.

The intermediate section, of which there is at least one, ensures a gradual transition in flexibility from the relatively stiff proximal section to the very flexible distal section. In order to be able to monitor the progress of the distal end of the catheter in a catheterization laboratory, a radiopaque band is placed on the distal section of the catheter to provide a visual x-ray image of the location of the distal end of the catheter.

The invention will be explained in greater detail with reference to the attached drawings, illustrating a catheter according to the invention in the vicinity of the heart and the brain of a patient:

BRIEF DESCRIPTION OF THE DRAWINGS

as illustrated in FIG. 1;

FIG. 3 illustrates an application of the catheter of the invention into vessels of the brain;

FIG. 4 shows the end-section of the catheter employed in FIG. 3.

DESCRIPTION OF THE PREFERRED EMBODIMENT

Figure 1:
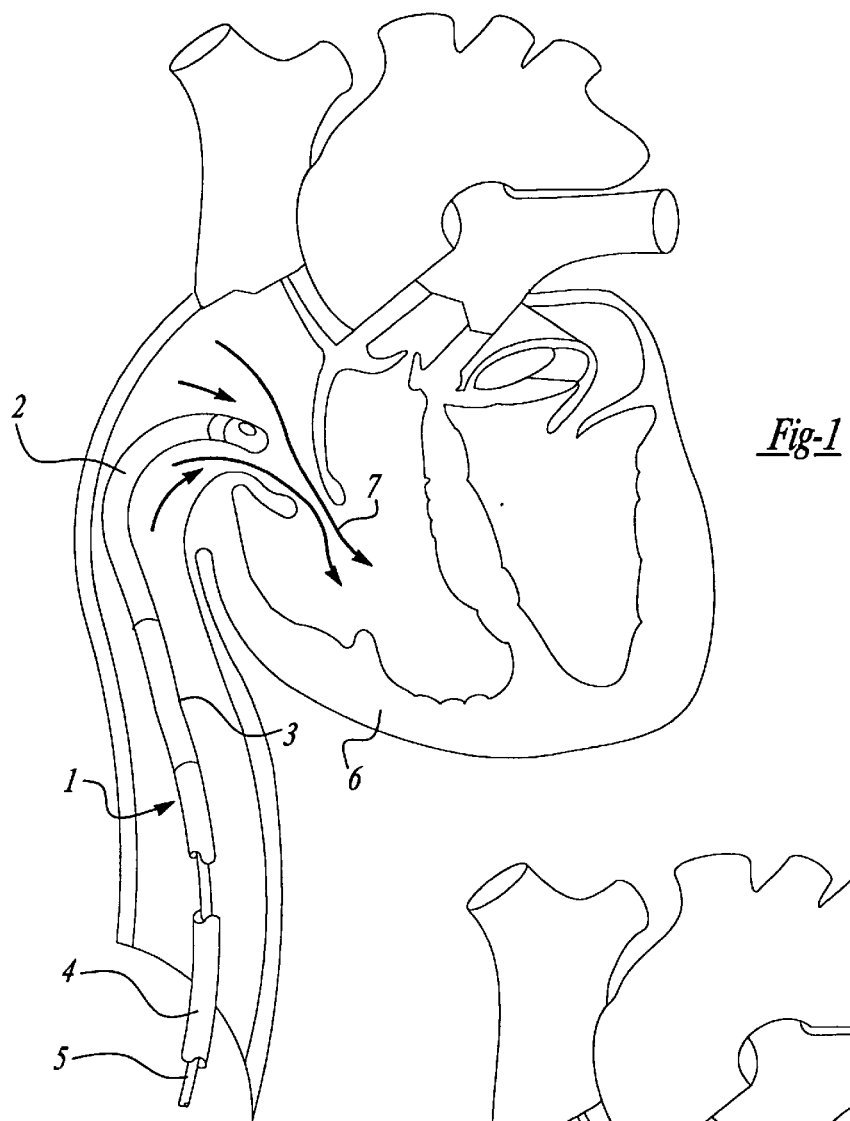
FIG. 1 illustrates a first phase of the introduction of an endovascular catheter according to the invention; and, FIG. 2 illustrates a final phase of the procedure.
Figure 2:
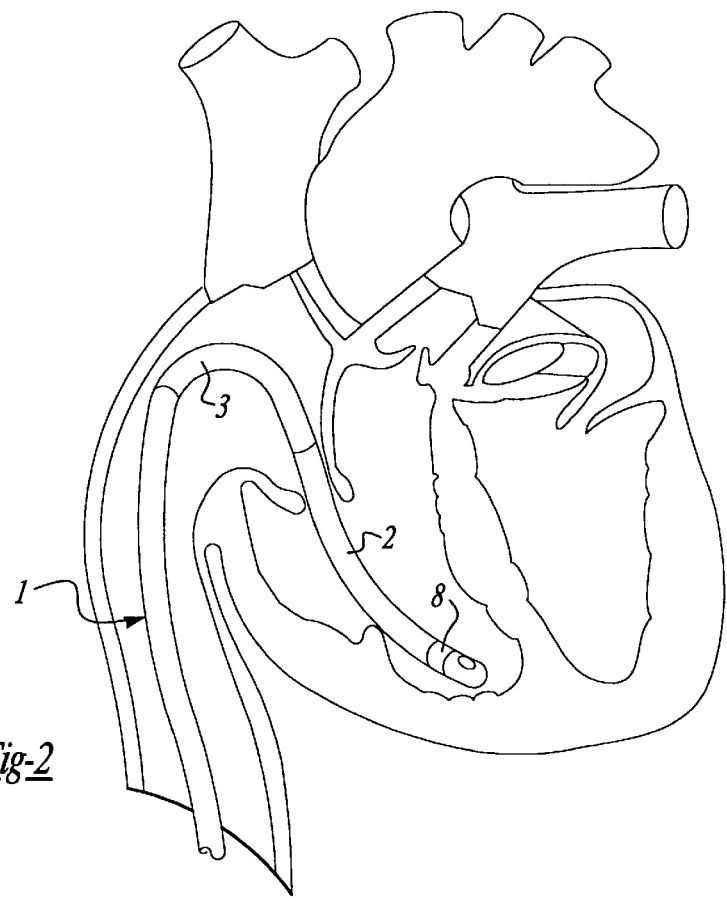

In FIGS. 1 and 2 the distal end portion of a catheter 1 according to the invention is shown. It comprises a tube like body portion 4, to which, via an intermediate section 3, and distal section 2 have been arranged. A lumen extends through the body portion 4, the intermediate section 3 and the distal section 2, inside of which a guidewire 5 can be received and through which for instance a diagnostic or treatment medium can be supplied to the distal end of the catheter.

The body portion 4 comprises at the proximal end, which has not been illustrated here, a connecting piece known as such, like for instance a Luer connector.

The distal section 2 of the catheter 1 according to the invention has been made pliable to such an extent that is does not retain its shape. As a result this distal section 2 is carried along and guided by the surrounding flow of blood within the vessel.

With the example of the embodiment illustrated in the figures, the distal section 2 of the catheter 1 is to be positioned in chamber of the heart 6. As has been indicated bu the arrows 7, blood enters on expansion of the chamber. The very flexible distal section 2 is carried along by this flow and as a result ends up inside the chamber of the heart 6, as has been illustrated in FIG. 2. A guidewire 5 can be used in order to introduce the catheter and in particular to guide the pliable distal section 2 to the vicinity of the desired position. Only during the last phase of introducing the catheter is the flexible distal section 2 released, as a result of which it may be carried along with the surrounding flow of blood.

Close to its relatively distal end, the distal section 2 has been provided with a radiopaque marker ring 8, which results in the distal end of the catheter being visible on an x-ray screen. The material of which the distal section 2 has been made may also comprise filler materials, as a result of which this end-section becomes visible in its entirely on an x-ray screen and/or under NMR conditions.

Although an embodiment of the catheter according to the invention can be used in the way illustrated in FIG. 3, the advantages of the invention are illustrated with respect to neuo-radiological applications. In that case the distal end of a catheter with a very small diameter, for instance of the order of 0.5 mm, is introduced into the vascular system 19 of the brain.

The catheter 10 shown in FIG. 3 is introduced through a hemostatic device 13 of a guiding catheter 11. Prior to that, the guiding catheter 11 has been advanced via the femoral artery and the aorta 20 of the patient into the carotid artery 21. From there the very flexible distal section 15 of the catheter may be carried along with the blood flow as far as the very small blood vessels of the brain.

As has been mentioned before, the catheter 10 has a very flexible distal section 15 which is bonded to a somewhat less flexible section 16, into the remaining part of the body portion 4. A lumen extends through the catheter which ends at the distal end in an end-opening 17. At the proximal end of the lumen is connected to a connection port 18 of the connecting member 14. Once the distal section of the catheter has arrived at the desired location, part of the vascular system in the vicinity of the distal section of the catheter can be visualized in a catheterization laboratory by means of supplying a contrast medium via the connection 18.

Although it has not been illustrated in detail in the figures, the catheter according to the invention may be fabricated, from the proximal towards the distal end, of the number of sections of decreasing stiffness. In particular the flexible distal section may be made up of two sections, whereby the length of the relatively distal section is about one quarter of that of the relatively proximal section.

Additionally, the distal section has been made in such a way that the diameter decreases towards the distal end. The decreasing diameter and decreasing stiffness towards the distal end ensure an improved good maneuverability of the catheter distal section.

As the catheter, or at least its distal section, is carried along by the blood flow, the advantages of a very traumatic treatment is achieved. Due to the small diameter of a catheter for such an application, a desired flexibility can easily be achieved, as a result of which the catheter distal section can be advanced into the very small and tortuous blood vessels of the brain of a patient. In conjunction with a small diameter, the end-section has a relatively large outside surface area, so that the impact of the surrounding flow on it can be relatively large as a result of which the end section is carried along easily into the small blood vessels. The catheter distal section can be advanced into the very small and tortuous blood vessels of the brain of the patient. As a result of the small diameter of the distal section an improved flexibility can be achieved.

Although the invention has been explained above with reference to an application-example in the vicinity of the heart and the brain, the invention is obviously not limited to catheters for use in these body organs. Also, for use in the vicinity of other organs, such as the liver and the kidneys, the invention has been found to be suitable for treatment.

The above description is conjunction with the attached drawings are for illustrative purposes only and are not intended to limit the scope of the invention, which is as defined in the claims below.

What is claimed is:

1. A non-balloon, flow-directed endovascular catheter that can be guided by blood flow within a vessel, wherein said catheter comprises:
   (a) a proximate elongate tubing segment having an inner lumen extending throughout the length thereof;
   (b) a distal elongate tubing segment having an inner lumen extending throughout the length thereof and being connected to an extending from the proximal tubing segment; wherein said proximal tubing segment is relatively stiff and said distal tubing segment is extremely flexible and has modules of elasticity less than 10 Newtons per square millimeter.

2. A catheter is defined in claim 1, wherein the distal tubing segment is of a smaller outside diameter than the proximal tubing segment.

3. A catheter as defined in claim 2, wherein the proximal tubing segment has a diameter in the range of 0.6 to 0.9 millimeters and the distal tubing segment has a diameter of in the range of 0.4 to 0.7 millimeters.

4. A catheter as defined in claim 3, wherein the proximal tubing segment has a length in the range of 10 to 30 centimeters and the distal tubing segment has a length in the range of 2 to 7 centimeters.

5. A catheter as defined in claim 4, wherein the proximal tubing segment has a higher burst pressure than the distal tubing segment.

6. A catheter as defined in claim 4, wherein the proximal tubing segment has a burst pressure of at least 200 pounds per square inch and the distal tubing segment has a burst pressure of least 190 pounds per square inch.

7. A catheter as defined in claim 6, wherein the distal tubing segment is comprised of polyethylene elastomers.

8. A catheter as defined in claim 6, wherein the distal tubing segment is compressed of polyvinyl chloride plasticized with polyurethane.

9. A catheter as defined in claim 8, wherein the distal tubing segment has a outer coating of polytetra fluoroethane.

10. A catheter as defined in claim 6, wherein the distal tubing segment is comprised of a styrene ethyl block styrene polymers.

11. A catheter as defined in claim 4, including an intermediate tubing segment interpased between the proximal tubing segment and the distal tubing segment, said intermediate tubing segment has the characteristic of being more flexible than the proximal tubing segment but less flexible than the distal tubing segment.

12. A catheter as defined in claim 11 including a distal tip portion connected to and extending from the distal tubing segment, said distal tip potion is comprised of a plastic formulation containing 30 to 80 weight percent of radiopaque agent so that the distal tip is more radiopaque than the other portions of the catheter.

* * * * *